United States Patent [19]

Gibson

[11] Patent Number: 5,440,061
[45] Date of Patent: Aug. 8, 1995

[54] HYDROLYSIS OF METHYL ESTERS IN DIMETHYLSULFOXIDE FOR PRODUCTION OF FATTY ACIDS

[75] Inventor: Michael S. Gibson, Loveland, Ohio

[73] Assignee: The Procter & Gamble Company, Cincinnati, Ohio

[21] Appl. No.: 219,066

[22] Filed: Mar. 29, 1994

[51] Int. Cl.⁶ .......................................... C07C 51/377
[52] U.S. Cl. .................................. 554/160; 554/161; 554/163; 554/154
[58] Field of Search ............... 554/160, 162, 163, 154, 554/161

[56] References Cited

U.S. PATENT DOCUMENTS

| | | | |
|---|---|---|---|
| 4,073,799 | 2/1978 | Kondo et al. | 260/345.8 P |
| 4,185,027 | 1/1980 | Logan | 260/415 |
| 4,335,263 | 6/1982 | Minai | 568/437 |
| 4,406,833 | 9/1983 | Boehme et al. | 260/123.7 |
| 4,981,966 | 1/1991 | Hermecz et al. | 544/229 |
| 4,996,098 | 2/1991 | Perusich et al. | 428/229 |
| 5,091,530 | 2/1992 | Hermecz et al. | 544/229 |
| 5,128,070 | 7/1992 | Sedelies et al. | 554/160 |

FOREIGN PATENT DOCUMENTS

| | | | |
|---|---|---|---|
| 1334205 | 10/1973 | United Kingdom | C07C 67/06 |
| 2146638 | 4/1985 | United Kingdom | C07C 27/02 |

*Primary Examiner*—José G. Dees
*Assistant Examiner*—Deborah D. Carr
*Attorney, Agent, or Firm*—Beth Goldstein Lewis

[57] ABSTRACT

The present invention relates to an improved process for preparing fatty acids from alkyl, preferably methyl esters comprising mixing the fatty acid ester with water, acid catalyst, and DMSO in order to form a single phase reaction mixture. The single phase reaction mixture is then heated to a temperature of from about 70° C. to about 130° C. to hydrolyze the fatty acid ester into the corresponding acid and volatile alcohol and removing the volatile alcohol. The acid catalyst is heat and water stable and the reaction mixture is essentially free of $C_2$–$C_5$ carboxylic acids. The initial stoichiometric ratio of the water to the ester is at least about 1:1.

26 Claims, 2 Drawing Sheets

HYDROLYSIS OF METHYL ESTERS IN DIMETHYLSULFOXIDE FOR PRODUCTION OF FATTY ACIDS

TECHNICAL FIELD

This invention relates to an improved process for hydrolyzing alkyl, preferably methyl, esters of fatty acids containing from about 5 to about 20 carbon atoms, preferably from about 5 to about 14 carbon atoms, into the corresponding fatty acids.

BACKGROUND OF THE INVENTION

Several methods for convening fatty acid methyl esters to fatty acids are known.

1. Saponification/Acidulation

This process is outlined below:

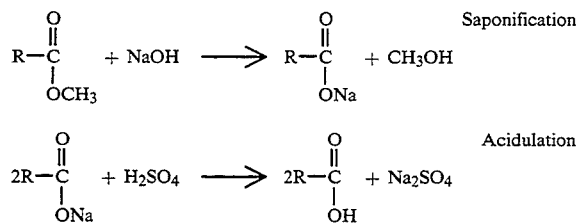

wherein R is a saturated or unsaturated aliphatic chain having from about 4 to about 19 carbon atoms.

The caustic and acid must be used in excess for achieving maximum conversion of ester to acid. The final product is obtained after washing, drying and distillation of the crude reaction mixture.

Disadvantages of this process include the high cost of processing chemicals, i.e., caustic and acid, the slowing of reaction rates with higher carbon chain length feedstock, and formation of intermediates, i.e., soap.

2. Acidolysis

This process involves reacting fatty acid and especially "light cut" fatty acid esters with a short chain carboxylic acid (e.g., propionic acid) in the presence of water and an acid catalyst as outlined below.:

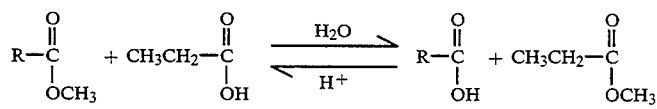

wherein R is defined above.

This is a well-known reaction and is described, for example, in Graves U.S. Pat. No. 1,882,808.

Methyl propionate removed from the acidolysis reaction can be reacted with water in the presence of catalyst to yield propionic acid and methanol. Unfortunately, methanol cannot be easily separated from unreacted propionate because of azeotrope formation, which requires costly high energy separation.

Very often, the acidolysis is an acetolysis. The replacing (displacing) acid is acetic acid. In the context of methyl esters of $C_5$-$C_{11}$ carboxylic acids, this means reacting such ester with acetic acid to produce $C_5$-$C_{11}$ carboxylic acids and methyl acetate. This reaction has the disadvantage in a commercial context of requiring disposal or separate hydrolysis of methyl acetate. Disposal is disadvantageous because consumed displacing acid is lost. Separate hydrolysis has the disadvantage of requiring a second process facility (reactor and distillation units different from the reactor and distillation units used for the acetolysis). Also, the acetic acid requires a drying step before it can be reused.

3. Basic Hydrolysis

This process involves splitting methyl esters into fatty acids and methanol at higher temperatures under pressure using catalytic amounts of basic materials. The soap formed initially will serve as emulsifying agent.

The disadvantages of this process are phase separation problems and high pressure operation.

4. Hydrolysis by Water

Conceptually esters can be hydrolyzed without catalyst at high pressures and temperatures, e.g., 700 psig and 250° C. The advantage of this process is that resulting products will not be contaminated with soap, acidic substances or other catalytic materials. The disadvantage is the high cost of equipment needed for high pressure operation.

5. Hydrolysis with Enzymes

Hydrolysis of esters can be promoted with enzymes. Enzymes will act as catalysts by emulsifying and hydrolyzing the reactants. The advantage of this process is that it produces light colored acids. The disadvantage of the process is partial completion of the hydrolysis reaction. In addition, the process control and to selection of enzymes will be critical for high catalytic activity.

SUMMARY OF THE INVENTION

The present invention provides an improved process of preparing fatty acids from alkyl, preferably methyl, esters via acid-catalyzed hydrolysis conducted in dimethyl sulfoxide (DMSO). In the acid hydrolysis process herein, alkyl, preferably methyl, esters of fatty acids are hydrolyzed into the corresponding fatty acids and a volatile alcohol in the presence of an acid catalyst and dimethyl sulfoxide. Since the ester and water are normally mutually insoluble, obtaining good contact between unhydrolyzed ester and water are critical in the process. The DMSO in this invention serves to aid the incorporation of water into the ester, or vice versa, and thereby provides an increased reaction rate. The present invention improves acid hydrolysis by using DMSO as an aid to form single phase reaction mixtures wherein the stoichiometric ratio of water to ester is at least about 1:1 on a molar basis.

Specifically, the process comprises the following steps:

(a) mixing fatty acid ester of a volatile alcohol with water, acid catalyst, and DMSO to form a single phase reaction mixture; and (b) heating the single phase reaction mixture to a temperature of from about 70° C. to about 130° C., to hydrolyze said fatty acid ester into the corresponding acid and volatile alcohol and removing said volatile alcohol, wherein the acid catalyst is heat and water stable, wherein the reaction mixture is essentially free of $C_2$-$C_5$, especially $C_2$-$C_4$ carboxylic acids, e.g., acetic, propionic and butyric acids; wherein the initial stoichiometric ratio of water to ester is at least about 1:1 on a molar basis; and wherein the initial molar ratio of any residual amount of carboxylic acid to ester is less than about 1:1, preferably less than about 0.5:1, especially when said carboxylic acid contains less than 6 carbon atoms (e.g., valeric acid).

Utilizing single phase reaction mixtures increases the rate of reaction, and maximizes the effect of the water that is present. The reaction is as follows:

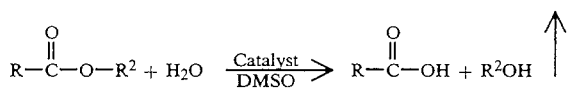

wherein R is a saturated or unsaturated aliphatic chain having from about 4 to about 19, preferably from about 4 to about 13, and more preferably from about 5 to about 11 carbon atoms; and wherein $R^2$ is a saturated or unsaturated aliphatic chain having from about 1 to about 4 carbon atoms, and is preferably a methyl group.

BRIEF DESCRIPTION OF THE DRAWINGS

While the Specification concludes with claims particularly pointing out and distinctly claiming the present invention, it is believed that the invention is better understood from the following description taken in conjunction with the associated drawings, in which:

Figure 1:
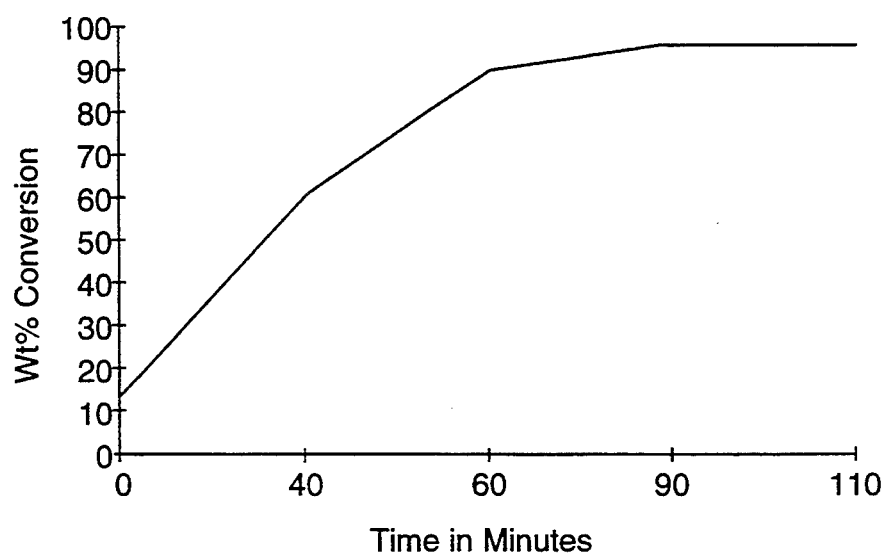
FIG. 1 is a graph showing HLAS catalyzed hydrolysis of light-cut methyl esters in DMSO.

The terms HLAS and DMSO are defined hereinafter.

DETAILED DESCRIPTION OF THE INVENTION

The present invention provides an improved process for preparing fatty acids from alkyl, preferably methyl, esters of fatty acids via acid-catalyzed hydrolysis conducted in the presence of dimethyl sulfoxide (DMSO) and water in order to form a single phase. The present invention improves acid hydrolysis by mixing water, fatty acid ester, acid catalyst, and DMSO to form a single phase reaction mixture wherein the initial stoichiometric ratio of water to ester is at least about 1:1 on a molar basis and wherein the initial molar ratio of any residual amount of carboxylic acid to ester is less than about 1:1, preferably less than about 0.5:1, especially when said carboxylic acid contains less than 6 carbon atoms Specifically, the process comprises the following steps:
 (a) mixing fatty acid ester of a volatile alcohol with water, acid catalyst and DMSO to form a single phase reaction mixture; and
 (b) heating the single phase reaction mixture to a temperature of from about 70° C. to about 130° C., to hydrolyze said fatty acid ester into the corresponding acid and volatile alcohol and removing said volatile alcohol,
wherein the acid catalyst is heat and water stable; wherein the initial molar ratio of any residual amount of carboxylic acid to ester is less than 1:1, preferably less than 0.5:1, especially where said carboxylic acid contains less than 6 carbon atoms; wherein the reaction mixture is essentially free of $C_2$-$C_5$, especially $C_2$-$C_4$ carboxylic acids; wherein the amount of fatty acid ester present is from about 5% to about 40%, preferably from about 8% to about 38%, and more preferably from about 10% to about 37% by weight of the reaction mixture; wherein the amount of acid catalyst present is from about 0.1% to about 40%, preferably from about 0.3% to about 20%, most preferably from about 0.5% to about 15% by weight of the reaction mixture; wherein the amount of DMSO present is from about 40% to about 80%, preferably from about 40% to about 75%, more preferably from about 44% to about 70% by weight of the reaction mixture; and wherein the amount of water present is from about 10% to about 25%, preferably from about 11% to about 20%, more preferably from about 11% to about 17% by weight of the reaction mixture. The following represents the preferred reaction of the present invention:

wherein R is a saturated or unsaturated aliphatic chain having from about 4 to about 19, preferably from about 4 to about 13, and more preferably from about 5 to about 11, carbon atoms. $R^2$ is a saturated or unsaturated aliphatic chain having from about 1 to about 4 carbon atoms, and is preferably a methyl group. Methyl esters are preferably used in the process of the present invention because the resulting alcohol is methanol, which is easier to remove. Specifically, light-cut methyl esters containing from about 8 to about 10 carbon atoms are the most preferred. Other esters can be used, especially if the resulting alcohol is useful for the end use of the fatty acid. Examples of suitable methyl esters include methyl caproate, methyl caprylate, methyl caprate, methyl laurate, methyl myristate, methyl myristoleate, methyl palmitate, methyl palmitoleate, methyl stearate, and methyl oleate. The methyl ester reactant herein can be a specific methyl ester or a mixture of different methyl esters. These compounds are essentially insoluble in water.

Catalyst

An acid catalyst is employed in the process of the present invention. The catalyst used should be highly acidic, heat and water stable, and be regenerable. The acid catalyst should not be a carboxylic acid since these tend to create the same problems mentioned above for acidolysis reactions.

Some of the preferred catalysts of the present invention are benzene sulfonic acid and linear alkyl benzene sulfonic acid (HLAS) of the formula:

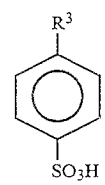

wherein $R^3$ is an alkyl chain having from 1 to about 20 carbon atoms, preferably from about 6 to about 14, more preferably from about 11 to about 13 carbon atoms; and mixtures thereof.

The $R^3$ group can be attached to the benzene ring at any carbon atom in the alkyl chain. But usually, the alkyl chain is attached to the benzene ring at approximately the middle carbon atom of the alkyl chain. The benzene ring can be substituted, e.g., with an additional methyl group.

Another preferred catalyst of the present invention is sulfuric acid, $H_2SO_4$. Sulfuric acid is one of the most widely used industrial chemicals in the United States. Since it is so widely available and fairly inexpensive, it is economically advantageous to use sulfuric acid as the acid catalyst of the present invention.

The acid catalyst level, by weight of the ester, is typically from about 0.1% to about 40%, preferably from about 0.3% to about 20%, more preferably from about 0.5% to about 15%, by weight of the reaction mixture. The acid catalyst is preferably recycled during the process.

The acid catalyst can be recovered by simple distillation of the resulting light cut acid away from the reaction mix. This can be accomplished by first removing the unreacted water, traces of methanol, DMSO, and any unreacted ester via vacuum distillation. The fatty acid product is then distilled under vacuum. The acid catalyst is left behind in the reaction vessel and can be directly recycled to the reaction. Temperature control is critical in this process to eliminate the decomposition of the catalyst during distillation. Temperatures should be less than about 163° C., preferably less than about 150° C. for the typical acid catalyst.

Water

The water in the reaction serves as both a reactant (see overall equation) and as a promoter for the acid catalyst to speed the reaction. This promoting effect is described in articles by Meade et al. at pages 1-6 of volume 39 of Journal of the American Oil Chemists' Society (January 1962). In general, less water is desirable since any remaining water must be removed. The amount of water present in the reaction is typically from about 10% to about 25%, preferably from about 11% to about 20%, more preferably from about 11% to about 17% by weight of the reaction mixture.

Process

Generally, the process of the present invention utilizes reaction temperatures of from about 70° C. to about 130° C., preferably from about 95° C. to about 125° C.

The pre-reaction mixture is preferably essentially free of $C_2$–$C_4$ carboxylic acids since these can react with the alcohol that is produced to form esters which can be more difficult to separate from the fatty acid product. (See Acidolysis, supra.)

The overall reaction is preferably carried out at atmospheric pressure. If desired, subatmospheric or superatmospheric pressures can be utilized. An increase in the pressure will increase water solubility in the ester layer.

The term "fatty acid" is used herein to mean carboxylic acid corresponding to the carboxylic acid portion of the ester reactant.

The process of the present invention can be carried out as a continuous system or batchwise, and is preferably carried out as a continuous system.

The following example illustrates, but does not limit, the present invention.

EXAMPLE

Procedure for Light-Cut Ester Hydrolysis Using (DMSO) as Solvent

Following is a batchwise procedure for hydrolyzing light-cut methyl esters.

Chemicals Required (added in this order)

1. About 41.5g methyl ester, 60%/40%, $C_{8/10}$ mixture
2. About 50 g distilled water
3. About 220 g DMSO
4. About 1.8 g HLAS or other organic or inorganic acid catalyst Procedure:

1. About 41.5 g of a mixture of $C_8$ and $C_{10}$ fatty acid methyl ester, about 50 g of distilled water, about 6.2 g of 98% $C_8$ fatty acid and about 200 ml DMSO are placed into an agitating flask fitted with a heating mantle, condenser and dropping funnel.
2. The mixture is heated to 125° C. while agitating. When boiling begins, about 1.8 g of HLAS is added.
3. A sample is taken from the flask for use as the "time zero" reference.
4. About 300 ml of distilled water is added over the course of the reaction through a dropping funnel.
5. Samples are taken at thirty minute intervals and reaction temperatures are monitored.
6. The samples of 3 and 5 are silylated with bis(trimethylsilyl)trifluoroacetamide in dichloromethane (50/50).
7. The samples of 6 are analyzed by gas chromatograph and a plot -LN (conversion) against time is developed.

FIG. 1 shows that after about two hours, conversion is greater than 98%, exhibiting a rate constant of 0.053 $min.^{-1}$. Atmospheric pressure is used.

The procedure of Example I is repeated with sulfuric acid replacing HLAS as the acid catalyst.

Figure 2:
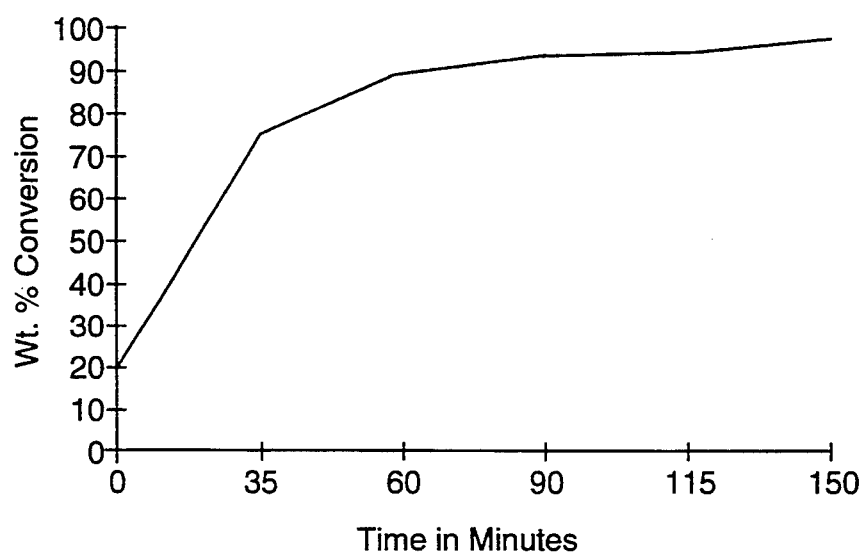
FIG. 2 is a graph showing sulfuric acid catalyzed hydrolysis of light-cut methyl estates in DMSO.

FIG. 2 shows that after about two hours the conversion rate is about 98% for the sulfuric acid catalyst as well.

What is claimed is:

1. A process for the production of fatty acids comprising the following steps:
    (a) mixing fatty acid ester of a volatile alcohol with water, acid catalyst, and DMSO to form a single phase reaction mixture; and
    (b) heating the single phase reaction mixture to a temperature of from about 70° C. to about 130° C. to hydrolyze said fatty acid ester into the corresponding acid and volatile alcohol and removing said volatile alcohol;

wherein the acid catalyst is heat and water stable; wherein the reaction mixture is essentially free of $C_2$–$C_5$ carboxylic acids; and wherein the initial stoichiometric ratio of water to ester is at least about 1:1 on a molar basis.

2. The process of claim 1 wherein the temperature in step (b) is from about 95° C. to about 130° C.

3. The process of claim 1 wherein the single phase reaction mixture is agitated.

4. The process of claim 1 wherein the acid catalyst is benzene sulfonic acid or linear alkyl benzene sulfonic acid of the formula:

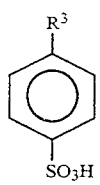

wherein $R^3$ is an alkyl chain having from 1 to about 20 carbon atoms, and mixtures thereof.

5. The process of claim 1 wherein the temperature in step (b) is from about 95° C. to about 130° C.

6. The process of claim 1 wherein the amount of fatty acid ester present in the reaction is from about 15% to about 40% by weight of the reaction mixture, the amount of acid catalyst present in the reaction is from about 0.1% to about 40% by weight of the reaction mixture, the amount of DMSO present in the reaction is from about 40% to about 80% by weight of the reaction mixture, and the amount of water present in the reaction is from about 10% to about 25% by weight of the reaction mixture.

7. The process of claim 6 wherein the single phase reaction mixture is agitated.

8. The process of claim 6 wherein the acid catalyst is benzene sulfonic acid or linear alkyl benzene sulfonic acid of the formula:

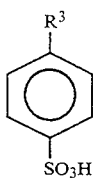

wherein $R^3$ is an alkyl chain having from 1 to about 20 carbon atoms, and mixtures thereof.

9. The process of claim 5 wherein the amount of fatty acid present in the reaction is from about 8% to about 38% by weight of the reaction mixture, the amount of acid catalyst present in the reaction is from about 0.3% to about 20% by weight of the reaction mixture, the amount of DMSO present in the reaction is from about 40% to about 75% by weight of the reaction mixture, and the amount of water present in the reaction is from about 11% to about 20% by weight of the reaction mixture.

10. The process of claim 9 wherein the temperature in step (b) is from about 95° C. to about 130° C.

11. The process of claim 9 wherein the single phase reaction mixture is agitated.

12. The process of claim 9 wherein the acid catalyst is benzene sulfonic acid or linear alkyl benzene sulfonic acid of the formula:

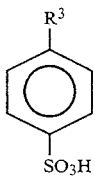

wherein $R^3$ is an alkyl chain having from 1 to about 20 carbon atoms, and mixtures thereof.

13. The process of claim 9 wherein the amount of fatty acid present in the reaction is from about 10% to about 37% by weight of the reaction mixture, the amount of acid catalyst present in the reaction is from about 0.5% to about 15% by weight of the reaction mixture, the amount of DMSO present in the reaction is from about 44% to about 70% by weight of the reaction mixture, and the amount of water present in the reaction is from about 11% to about 17% by weight of the reaction mixture.

14. The process of claim 13 wherein the temperature in step (b) is from about 95° C. to about 130° C.

15. The process of claim 13 wherein the single phase reaction mixture is agitated.

16. The process of claim 14 wherein the acid catalyst is benzene sulfonic acid or linear alkyl benzene sulfonic acid of the formula:

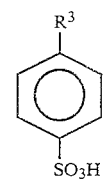

wherein $R^3$ is an alkyl chain having from 1 to about 20 carbon atoms, and mixtures thereof.

17. The process of claim 16 wherein $R^3$ is an alkyl group with from about 6 to about 14 carbon atoms, and mixtures thereof.

18. The process of claim 17 wherein $R^3$ is an alkyl group having from about 11 to about 13 carbon atoms, and mixtures thereof.

19. The process of claim 18 wherein the $R^3$ group is attached to the benzene ring at the middle one-half of the alkyl chain.

20. The process of claim 1 wherein the acid catalyst is sulfuric acid.

21. The process of claim 1 wherein said fatty acid ester has the formula:

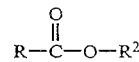

wherein R is a saturated or unsaturated aliphatic chain having from about 4 to about 19 carbon atoms, and $R^2$ is a saturated or unsaturated aliphatic chain having from about 1 to about 4 carbon atoms.

22. The process of claim 21 wherein R is from about 4 to about 13 carbon atoms, and $R^2$ is from about 1 to about 2 carbon atoms.

23. The process of claim 22 wherein R is from about 5 to about 11 carbon atoms, and $R^2$ is a methyl group.

24. The process of claim 1 wherein the acid catalyst is recovered from the reaction mixture by the following steps:

(a) distilling the unreacted water, alcohol, DMSO and unreacted ester under vacuum; and
(b) distilling the fatty acid product away from the product of (a) under vacuum.

25. The process of claim 24 wherein the temperature does not exceed about 163° C. for reaction mixtures containing esters of $C_8$–$C_{12}$ fatty acids.

26. The process of claim 25 wherein the temperature does not exceed about 150° C.

* * * * *